(12) United States Patent
Lalain et al.

(10) Patent No.: US 9,347,860 B1
(45) Date of Patent: May 24, 2016

(54) APPARATUS FOR TESTING VAPOR EMISSIONS FROM MATERIALS

(71) Applicant: U.S. Army Edgewood Chemical and Biological Command, APG, MD (US)

(72) Inventors: Theresa A. Lalain, Bel Air, MD (US); Brent A. Mantooth, Bel Air, MD (US); Corey L. Piepenburg, Nottingham, MD (US)

(73) Assignee: The United States of America as Represented by the Secretary of the Army, Washington, DC (US)

( * ) Notice: Subject to any disclaimer, the term of this patent is extended or adjusted under 35 U.S.C. 154(b) by 207 days.

(21) Appl. No.: 14/166,170

(22) Filed: Jan. 28, 2014

Related U.S. Application Data

(60) Provisional application No. 61/791,292, filed on Mar. 15, 2013.

(51) Int. Cl.
*G01N 1/22* (2006.01)
*G01N 33/00* (2006.01)

(52) U.S. Cl.
CPC .......... *G01N 1/2226* (2013.01); *G01N 33/0009* (2013.01); *G01N 2001/2241* (2013.01)

(58) Field of Classification Search
CPC ............... G01N 1/2226; G01N 2001/2241; G01N 2001/383; G01N 2001/2223; G01N 2001/045; G01N 33/0021; G01N 2035/00356; G01N 2035/00396
See application file for complete search history.

(56) References Cited

U.S. PATENT DOCUMENTS

| | | | | |
|---|---|---|---|---|
| 4,981,046 A * | 1/1991 | Lawrence | ................. | B01L 5/02 73/865.6 |
| 5,051,240 A * | 9/1991 | Nakai | ................ | G01N 33/0009 422/536 |
| 5,147,418 A * | 9/1992 | Laverman | .............. | B65D 90/30 220/227 |
| 5,345,809 A * | 9/1994 | Corrigan | .............. | G01N 1/2214 250/286 |
| 5,502,998 A * | 4/1996 | Miller | .................. | G01N 1/2273 73/1.06 |
| 5,705,223 A * | 1/1998 | Bunkofske | .......... | H01L 21/6715 118/52 |
| 6,073,499 A * | 6/2000 | Settles | ................. | G01N 1/2214 73/864.34 |
| 6,656,017 B2 * | 12/2003 | Jackson | ................ | B08B 7/0092 134/10 |
| 7,051,573 B2 * | 5/2006 | Bresciani | ........... | G01N 33/0009 73/23.2 |
| 7,942,033 B2 * | 5/2011 | Jenkins | ................ | G01N 1/2205 73/31.01 |

(Continued)

OTHER PUBLICATIONS

Lalain, Teri, et al. Chemical Contaminant and Decontaminant Test Methodology Source Document. No. ECBC-TR-980. Army Edgewood Chemical Biological Center APG MD Research and Technology Dir, Jul. 2012.*

(Continued)

*Primary Examiner* — Lisa Caputo
*Assistant Examiner* — Punam Roy
(74) *Attorney, Agent, or Firm* — Ulysses John Biffoni

(57) ABSTRACT

An apparatus comprising a dynamic vapor microchamber having a recessed area that accommodates a test material that includes chemical vapors emitted therefrom; an air inlet chamber that directs a flow of air towards the recessed area; at least one air flow wall adjacent to the recessed area and intersecting the flow of air, wherein the at least one air flow wall disrupts the air flow field as it flows towards the test material and produces a uniform and distributed laminar air flow field across a surface of the test material; a thermal controller under the recessed area that maintains a uniform temperature of the test material and the flow of air over the test material; and an air exhaust port that collects the vapors emitted from the test material. The apparatus may include a plurality of chambers arranged adjacent to one another.

19 Claims, 3 Drawing Sheets

(56) References Cited

U.S. PATENT DOCUMENTS

| | | | | |
|---|---|---|---|---|
| 8,742,334 | B2* | 6/2014 | Molloy | H01J 49/105 204/157.41 |
| 2004/0244465 | A1* | 12/2004 | Bresciani | G01N 33/0009 73/23.34 |
| 2011/0239738 | A1* | 10/2011 | Bisschops | G01N 1/22 73/23.42 |
| 2013/0162991 | A1* | 6/2013 | O'Connor | G01J 3/0291 356/317 |
| 2014/0223991 | A1* | 8/2014 | Hilliard | G01N 1/2226 73/23.2 |

OTHER PUBLICATIONS

Lalain, Teri. Small-Item Vapor Test Method, FY11 Release. No. ECBC-TR-933. Army Edgewood Chemical Biological Center APG MD Research and Technology Dir, Jul. 2012.*

Willis, Matthew P., Brent A. Mantooth, and Teri A. Lalain. "Novel methodology for the estimation of chemical warfare agent mass transport dynamics. Part II: absorption." The Journal of Physical Chemistry C 116.1 (2011): 546-554.*

Lalain, Teri, et al. Chemical Warfare Agent Decontamination Efficacy Testing Large-Scale Chamber mVHP (registered trademerk) Decontamination System Evaluation. No. ECBC-TR-731. Edgewood Chemical Biological Center Aberdeen Proving Ground MD, 2010.*

Magee, R. J., et al. "VOC Emissions from building materials—the impact of specimen variability—a case study." Indoor air quality problems and engineering solutions (Research Triangle Park, NC Jul. 21, 2003) (2003): 1-17.*

Standard Guide for Small-scale Environmental Chamber Determinations of Organic Emissions from Indoor Materials/Products, ASTM D:5116-10; American Society for Testing of Materials, USA (2010).*

* cited by examiner

APPARATUS FOR TESTING VAPOR EMISSIONS FROM MATERIALS

CROSS-REFERENCE TO RELATED APPLICATIONS

This application claims the benefit of U.S. Provisional Application No. 61/791,292, filed on Mar. 15, 2013, the complete disclosure of which, in its entirely, is hereby incorporated by reference.

GOVERNMENT INTEREST

The invention described herein may be manufactured, used, and/or licensed by or for the United States Government.

BACKGROUND

1. Technical Field

The embodiments herein generally relate to the measurement of chemical vapor emissions from materials, and more particularly to the detection and measurement of very small chemical vapor emissions from materials.

2. Description of the Related Art

Evaluating the emission of chemical vapors from materials is investigated for a wide range of materials and emitting chemicals. For instance, measuring and characterizing vapor emissions over time is important for materials that are manufactured using various chemical treatments or processes such as plasticizers, adhesives, and polymerization. The nature of the material and reason for performing the emission measurement contributes to how the chemical vapor emission is measured. Conventional dynamic vapor chambers utilize a cylindrical geometry with impinging jet air flow to contain the material and emitting vapors. However, the chamber geometry and air flow typically do not provide the controlled environment required to fully characterize the dynamic processes of vapor emissions for applications such as the contamination and decontamination of materials with, for example, chemical warfare agents. Accordingly, it is desirable to have a new and improved apparatus for testing small vapor emissions from materials.

SUMMARY

In view of the foregoing, an embodiment herein provides an apparatus comprising a chamber having a recessed area that accommodates a test material, wherein the test material includes vapors emitted therefrom; an air inlet chamber that directs at flow of air towards the recessed area; at least one air flow wall adjacent to the recessed area and intersecting the flow of air, wherein the at least one air flow wall disrupts the air flow field as it flows towards the test material and produces a uniform and distributed laminar air flow field across a surface of the test material; a thermal controller under the recessed area that maintains a uniform temperature of the test material and the flow of air over the test material; and an air exhaust port that collects the vapors emitted from the test material. The thermal controller may comprise a thermal exchange liquid. The air volume in the chamber may comprise approximately 30 mL of air. The apparatus may further comprise a plurality of chambers arranged adjacent to one another. The chamber may comprise a lid that provides an air tight seal around the recessed area. The apparatus may further comprise a groove surrounding the recessed area; and a sealing ring or gasket positioned within the groove and contacting the lid when the lid is pushed towards the recessed area. The apparatus may further comprise a pair of air flow walls positioned on opposite sides of the recessed area.

Another aspect of the embodiments herein provides a dynamic vapor microchamber comprising a section adapted to accommodate a test material; an air inlet chamber that directs a flow of air towards the section: an air flow wall proximate to the section and positioned to intersect the flow of air, wherein the air flow wall controls the air flow field as it moves over the test material and produces a uniform and distributed laminar air flow field across a surface of the test material; a thermal controller adjacent to the section that controls a temperature of the test material and the air over the test material; and an air exhaust port that transmits vapors emitted from the test material. The thermal controller may comprise a thermal exchange liquid. The air volume in the microchamber may comprise approximately 30 mL of air. The dynamic vapor microchamber may further comprise a lid that provides an air tight seal around the section. The dynamic vapor microchamber may further comprise a groove surrounding the section; and a sealing ring or gasket positioned within the groove and contacting the lid when the lid is directed towards the section. The dynamic vapor microchamber may further comprise a pair of air flow walls positioned on opposite sides of the section.

Another aspect of the embodiments herein provides a method of measuring vapor emissions from materials, the method comprising positioning a test material including a chemical in a vapor microchamber having a recessed area that accommodates the test material; directing a flow of air towards the test material; controlling the flow of air moving over the test material by producing a uniform and distributed laminar air flow field across a surface of the test material; controlling a temperature of the test material and the flow of air over the test material; wherein the test material emits chemical vapors; collecting the vapors emitted from the test material; and determining vapor emission rates of the chemical from the material. The method may further comprise controlling the temperature using a thermal exchange liquid. The method may further comprise calculating vapor concentrations of the chemical. The method may further comprise arranging a plurality of the vapor microchambers adjacent to one another. The method may further comprise sealing the recessed area. The method may further comprise using an air flow wall to control the air flow field. The method may further comprise using a pair of air flow walls positioned on opposite sides of the recessed area to control the air flow field.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which.

DETAILED DESCRIPTION OF PREFERRED EMBODIMENTS

Figure 1A:
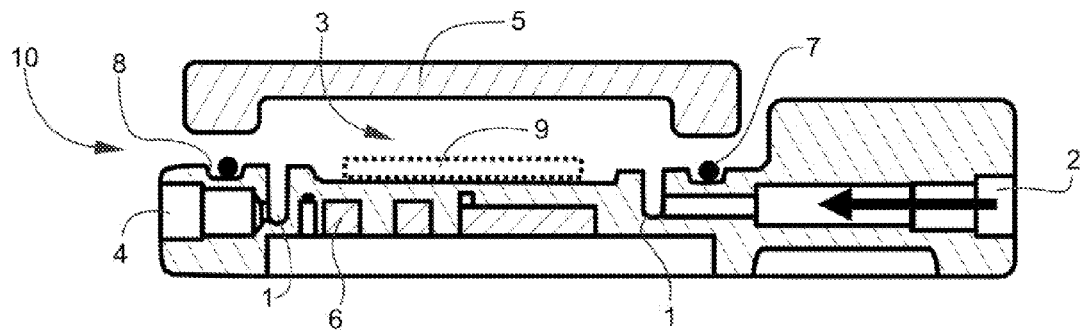
FIG. 1A illustrates a side view of a dynamic vapor microchamber according to an embodiment herein.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of was in which the embodiments herein may be practiced and to further enable those of skill in the art to practice the embodiments herein. Accordingly, the examples should not be construed as limiting the scope of the embodiments herein.

The embodiments herein provide a dynamic vapor microchamber that enables the time-resolved measurement of chemical vapor emissions from materials. The dynamic vapor microchamber allows for the control of all relevant aspects of the measurement of vapor emission. Referring now to the drawings, and more particularly to FIGS. 1A through 3, where similar reference characters denote corresponding features consistently throughout the figures, there are shown preferred embodiments.

The dynamic vapor chamber 10 provided by the embodiments herein may be used for applications such as the characterization of contamination of materials 9, the decontamination of chemicals from materials, the development of chemically hardened paints or materials, the characterization of chemical interactions with personal protective equipment materials, etc., for example, but is not limited to these applications. The internal volume of the dynamic vapor chamber 10 is typically on the order of $1\times10^{-6}$ $m^3$ although other dimensions and configurations are possible in accordance with the embodiments herein.

One example application of the dynamic vapor microchamber 10 is for materials that are manufactured with various chemical treatments or processes (e.g., plasticizers, adhesives, and polymerization) and the interest is to characterize the emission of various chemicals over a specified time period. Typically, a sample of the material 9 is placed in the recessed area 3 of the microchamber 10 and airflow is directed through the chamber enclosure as vapors are emitted from the material 9. Calculation procedures are used to determine vapor emission rates of the chemical from the material 9 so that concentrations of the chemical can be predicted in other situations or environments. The predicted calculations are used to perform analyses such as risk assessments to determine the level of chemical exposure to people residing in the specified situation.

Figure 1B:
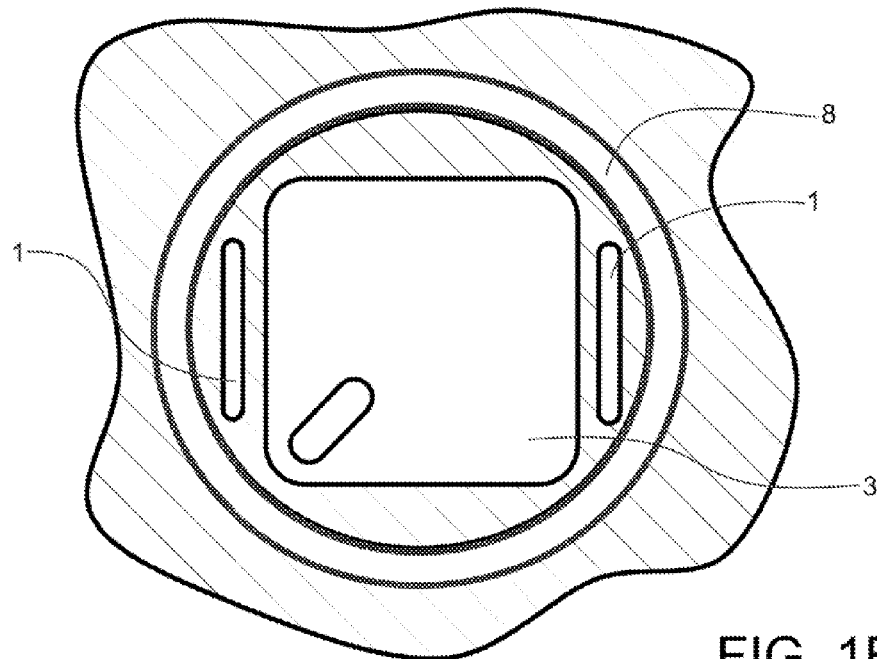
FIG. 1B illustrates a top view of the dynamic vapor microchamber of FIG. 1A according to an embodiment herein.
Figure 2:
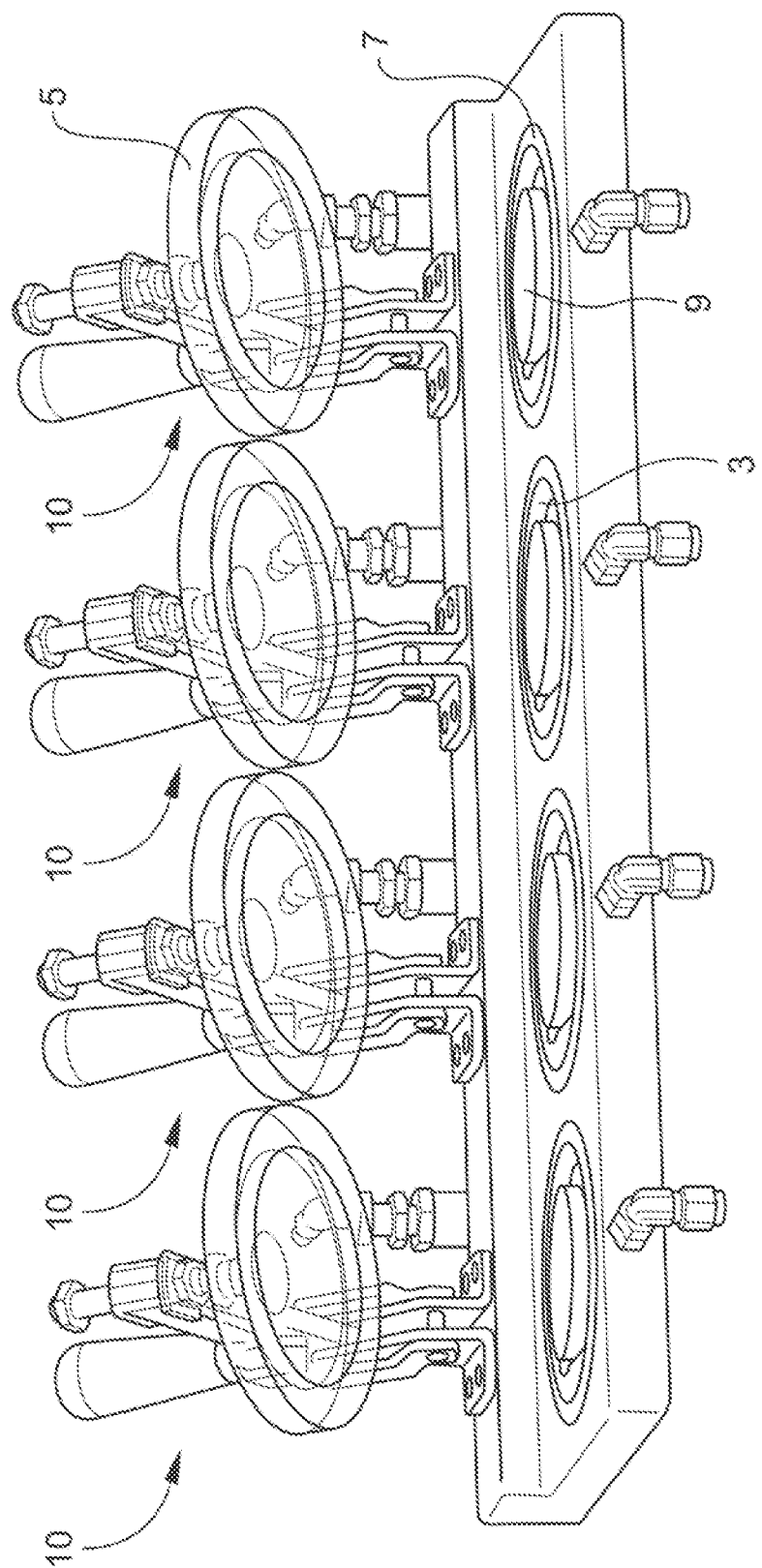
FIG. 2 illustrates a perspective view of multiple dynamic vapor microchambers according to an embodiment herein.

As mentioned above, the dynamic vapor microchamber 10 allows for the control of all relevant aspects of the measurement of vapor emission as illustrated in FIGS. 1A and 1B. The dynamic vapor microchamber 10 is configured to control temperature using a thermal exchange liquid 6 positioned under said recessed area 3, and facilitates material geometries applicable to material vapor emission such as that used in contamination and decontamination testing of materials. The geometrical configuration of the dynamic vapor microchamber 10 is designed to produce a distributed laminar air flow field across the surface of the test material 9 through the use of an air flow wall 1 to disrupt the impinging jet (air) flow (denoted by the arrow in FIG. 1A) from the chamber air inlet 2. The air then flows across the material 9, resting in the test material recessed area 3. The geometrical configuration of the dynamic vapor microchamber 10 results in a very small air volume (on the order of approximately 30 mL), providing very high sensitivity to measure vapor emissions from the test material 9. The dynamic vapor microchamber 10 is configured as an individual test unit; however one or more test units may be constructed and used simultaneously as shown in FIG. 2.

The dynamic vapor microchamber 10 is used by placing a material of interest 9 in the dynamic vapor microchamber 10, sealing the chamber lid 5, and initiating air flow through the microchamber inlet 2. Vapor samples are collected from the exhaust port 4 of the dynamic vapor microchamber 10. Vapor samples are quantified using various quantitative analytical techniques to enable the calculation of vapor concentrations and vapor emission rates of the test material 9. The temperature control approach facilitates uniform temperature of the test material 9 and air flowing into the dynamic vapor microchamber 10. This mediates temperature gradients in the test chamber 10, which may influence the experimental results.

The geometrical configuration of the dynamic vapor microchamber 10 results in flow field that develops a uniform, laminar boundary layer across the surface of the test material 9, as compared to impinging jet configurations that provide non-uniform boundary layers across the surface of the material 9. The boundary layer uniformity and air velocity at the surface of the material 9 influence the measured vapor emission. The combination of these features provides as reproducible, high sensitivity dynamic vapor microchamber 10 that enables a reproducible, robust, and highly sensitive measurement of vapor emissions.

The preferred material of construction is stainless steel 316L due to its chemically inert characteristics. It is preferable, but not required, that the apparatus 10 is constructed of any inert, nonabsorptive material such as most metals (e.g., steel, aluminum) or glass. The embodiments herein may be constructed of a single microchamber 10 (as in FIGS. 1A and 1B) or in groups of multiple microchambers 10 (as in FIG. 2). The closure system (e.g., closure lid 5) is preferred, but not required, to provide an air tight seal to enclose the test material 9 within the chamber 10. An o-ring 7 resting in an o-ring groove 8 further facilitates the air tight seal upon closure of the lid 5. The air wall may be any depth or width to ensure the impinging jet flow from the inlet 2 is disrupted to a laminar flow across the material 9.

Figure 3:
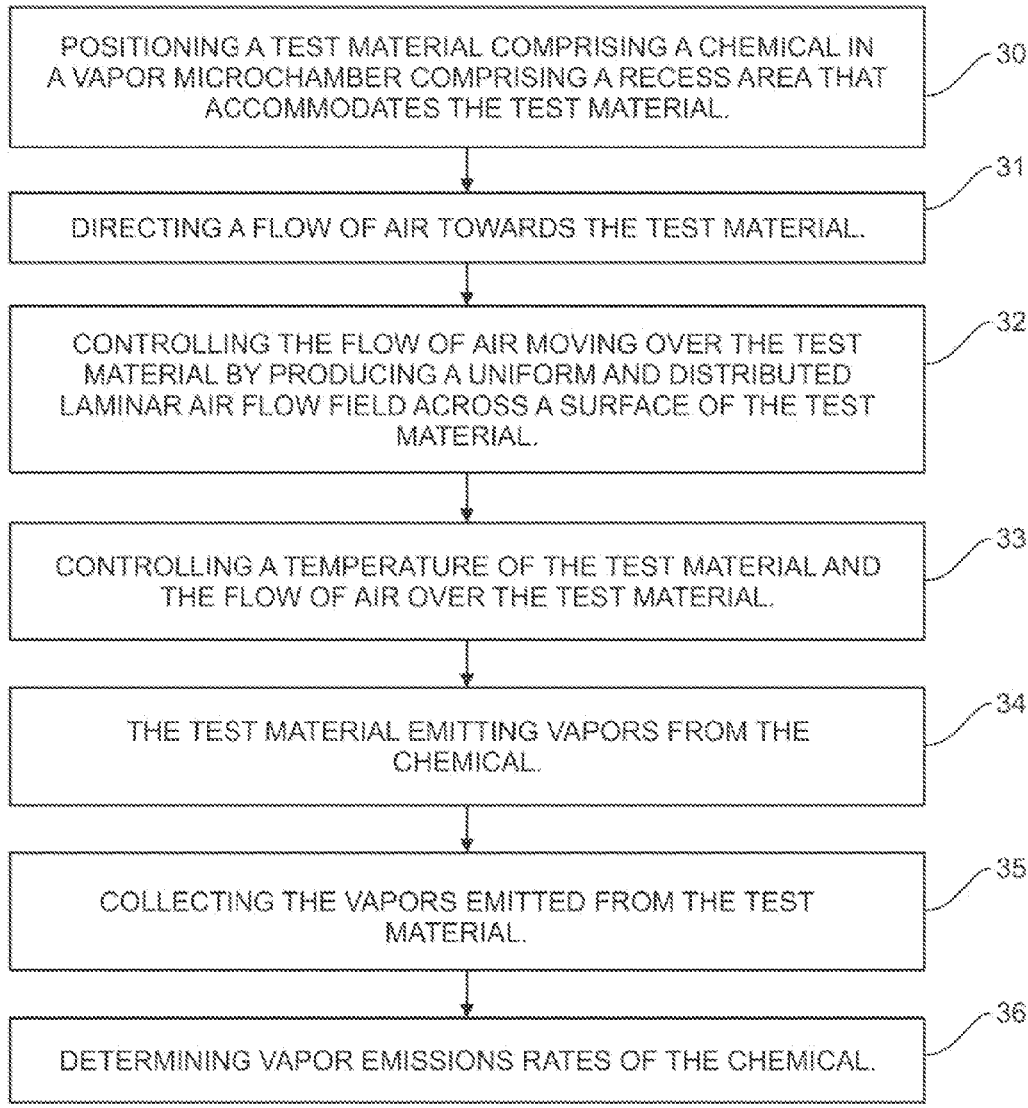
FIG. 3 is a flow diagram illustrating a method according to an embodiment herein.

FIG. 3, with reference to FIGS. 1A through 2, is a flow diagram illustrating a method of measuring vapor emissions from materials 9 according to an embodiment herein. With reference to FIG. 3, the method comprises positioning (30) a test material 9 including a chemical (not shown) in a vapor microchamber 10 having a recessed area 3 that accommodates the test material 9; directing (31) a flow of air towards the test material 9; controlling (32) the flow of air moving over the test material 9 by producing a uniform and distributed laminar air flow field across a surface of the test material 9; controlling (33) a temperature of the test material 9 and the flow of air over the test material 9; the test material 9 emitting (34) vapors from the chemical; collecting (35) the vapors emitted from the test material 9; and determining (36) vapor emission rates of the chemical. The method may further comprise controlling the temperature using a thermal exchange liquid 6. The method may further comprise calculating vapor concentrations of the chemical. The method may further comprise arranging a plurality of the vapor microchambers 10 adjacent to one another. The method may further comprise sealing the recessed area. The method may further comprise using an air flow wall 1 to control the air flow field. The method may further comprise using a pair of air flow walls 1 positioned on opposite sides of the recessed area 3 to control the air flow field.

The foregoing description of the specific embodiments will so fully reveal the general nature of the embodiments herein that others can, by applying current knowledge, readily modify and/or adapt for various applications such specific embodiments without departing from the general concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

What is claimed is:

1. An apparatus for testing vapor emissions from materials, comprising:
    a chamber having a recessed area that accommodates a test material, wherein said test material may emit chemical vapors emitted therefrom;
    an air inlet chamber that directs a flow of air towards said recessed area and is positioned below said recessed area so that the test material positioned above the air inlet;
    at least one air flow wall adjacent to and extending below said recessed area and intersecting said flow of air from said air inlet, wherein said at least one air flow wall disrupts said air flow field as it flows towards said test material and produces a uniform and distributed laminar air flow field across a surface of said test material;
    a thermal controller under said recessed area that maintains a uniform temperature of said test material and said flow of air over said test material; and
    an air exhaust port that collects said vapors emitted from said test material.

2. The apparatus of claim 1, wherein said thermal controller comprises a thermal exchange liquid.

3. The apparatus of claim 1, wherein an air volume in said chamber comprises approximately 30 mL of air.

4. The apparatus of claim 1, further comprising a plurality of chambers arranged adjacent to one another.

5. The apparatus of claim 1, wherein said chamber includes a lid that provides an air tight seal around said recessed area.

6. The apparatus of claim 5, further comprising:
    a groove surrounding said recessed area; and
    a sealing ring positioned within said groove and contacting said lid when said lid is pushed towards said recessed area.

7. The apparatus of claim 1, wherein said at least one air flow wall comprises a pair of air flow walls positioned on opposite sides of said recessed area.

8. A dynamic vapor microchamber, comprising:
    a section adapted to accommodate a test material;
    an air inlet chamber positioned below said section that directs a flow of air towards said section;
    an air flow wall proximate to and extending below said section and positioned to intersect said flow of air, wherein said air flow wall controls said air flow field as it moves over said test material and produces a uniform and distributed laminar air flow field across a surface of said test material;
    a thermal controller adjacent to said section that controls a temperature of said test material and said flow of air over said test material; and
    an air exhaust port that transmits vapors emitted from said test material.

9. The dynamic vapor microchamber of claim 8, wherein said thermal controller comprises a thermal exchange liquid.

10. The dynamic vapor microchamber of claim 8, wherein an air volume in the microchamber comprises approximately 30 mL of air.

11. The dynamic vapor microchamber of claim 8, further comprising a lid that provides an air tight seal around said section.

12. The dynamic vapor microchamber of claim 11, further comprising:
    a groove surrounding said section; and
    a sealing ring positioned within said groove and contacting said lid when said lid is directed towards said section.

13. The dynamic vapor microchamber of claim 8, further comprising a second air flow wall positioned on a side of said section opposite to said airflow wall.

14. A method of measuring vapor emissions from materials, said method comprising:
    positioning a test material including a chemical in a vapor microchamber having a recessed area that accommodates said test material, said test material emitting vapors of said chemical over time;
    directing a flow of air towards said test material from an air inlet positioned below said recessed area;
    controlling said flow of air moving over said test material by producing a uniform and distributed laminar air flow field across a surface of said test material by intersecting said flow of air from said air inlet with an air flow wall;
    controlling a temperature of said test material and said flow of air over said test material;
    collecting said vapors emitted from said test material; and
    determining vapor emission rates of said chemical.

15. The method of claim 14, further comprising controlling said temperature using a thermal exchange liquid.

16. The method of claim 14, further comprising calculating vapor concentrations of said chemical.

17. The method of claim 14, further comprising arranging a plurality of said vapor microchambers adjacent to one another.

18. The method of claim 14, further comprising sealing said recessed area.

19. The method of claim 14, further comprising using a pair of air flow walls positioned on opposite sides of said recessed area to control said air flow field.

* * * * *